United States Patent [19]
Mori et al.

[11] Patent Number: 5,665,742
[45] Date of Patent: Sep. 9, 1997

[54] BATH MEDICINE COMPOSITION AND ITS USE IN INHIBITING THE GENERATION OF BODY ODOR

[75] Inventors: Shinobu Mori, Kanuma; Wataru Okawa; Hidenori Yorozu, both of Utsunomiya, all of Japan

[73] Assignee: Kao Corporation, Tokyo, Japan

[21] Appl. No.: 448,774

[22] Filed: May 24, 1995

[30] Foreign Application Priority Data

May 31, 1994 [JP] Japan .................. 6-118062

[51] Int. Cl.$^6$ .............. A61K 31/44; A61K 31/17; A61K 31/14; A61K 31/075
[52] U.S. Cl. .............. 514/358; 514/596; 514/643; 514/721
[58] Field of Search .................. 514/340, 721, 514/643, 358, 596

[56] References Cited

U.S. PATENT DOCUMENTS

| | | | |
|---|---|---|---|
| 4,686,211 | 8/1987 | Hara et al. | 514/148 |
| 4,766,113 | 8/1988 | West et al. | 514/187 |

OTHER PUBLICATIONS

Database WPI, Derwent Info. Ltd., AN-88-036416/05, JP-63-043665, Feb. 24, 1988.

Primary Examiner—James J. Seidleck
Assistant Examiner—Michael A. Williamson
Attorney, Agent, or Firm—Oblon, Spivak, McClelland, Maier & Neustadt, P.C.

[57] ABSTRACT

The generation of body odor can be easily inhibited effectively without necessitating any troublesome operation such as coating and spraying by using a bath medicine composition containing at least one germicide (A) selected from the group consisting of phenolic germicides, cationic germicides and trichlorocarbanilide and a carbon dioxide generating component (B) in bathing.

14 Claims, No Drawings

BATH MEDICINE COMPOSITION AND ITS USE IN INHIBITING THE GENERATION OF BODY ODOR

BACKGROUND OF THE INVENTION

1. Field of the Invention

The present invention relates to a bath medicine composition which comprises a specific germicide and a carbon dioxide generating component and exhibits an excellent body deodorant effect, and to a method for inhibiting the generation of body odor with the bath medicine composition.

2. Discussion of the Background

Many external preparations are known for preventing or reducing body odor, most of which usually contain an antisudorific, a germicide, a masking agent as an odoriferous component, and an adsorbent for odoriferous components. These preparations are locally applied to various body parts, such as the armpit or foot.

The antisudorific is a substance having the activity of lowering sweat rate also as known as antiperspirant. Representative examples of antisudorifics include aluminum compounds which are also astringent agents, among which aluminum chloride is commonly used.

The germicide is a substance which causes inhibition of the growth of microbes causative of tragomaschalia. Examples of such germicides include hexachlorophene and various quaternary ammonium compounds.

The masking agent is a substance having a comfortable smell, such as eugenol.

Examples of conventional adsorbents for odoriferous components include zinc oxide, activated carbon and zeolite (see Japanese Patent Publication-A No. 63-43665).

Common antisudorifics help to lower the rate of sweat, which is a source of sweat odor. However, they have also a disadvantage in that they cannot completely inhibit sweat from a physiological standpoint. Additionally, they are only marginally effective against strong body odor.

Common germicides exhibit a local deodorant effect when applied to body areas, such as the armpit or foot as an external preparation. However, the effect is only temporary and does not persist. Further, it is not practical to attempt to apply an external preparation to the entire body. Furthermore, even if the germicide is applied to the entire body in the form of a cleaner composition, it will not remain on the skin in an effective concentration and will thus fall to provide a sufficient effect.

Masking agents have a disadvantage that their smells can intermingle with body odor to result in unpleasant odors in some cases.

Adsorbents are ineffective for high-boiling components of sweat and body odor, which are one of the causes of tragomaschalia. However, they do have a high effect on low-boiling components such as lower fatty acids.

Accordingly, conventional external preparations for preventing or reducing body odor do not provide sufficient and effective prevention of tragomaschalia.

Meanwhile, household bath medicine compositions containing germicides are also known [see U.S. Pat. No. 5,182,105 (published on Jan. 28, 1993, assignee: Kao Corporation)]. However, such germicides are used for the purpose of antisepsis, so that the contents thereof are extremely low.

Further, there are also some germicide-containing bath medicine compositions available for specific medical uses. For example, Japanese Patent Publication-A No. 54-32636 (published on Mar. 10, 1979) discloses a bath medicine composition for the treatment of dermatomycosis such as tinea pedis, ring worm and tinea cruris, which comprises salicylic acid as the base germicide, and benzoic acid and thymol as other germicides, and, further, contains an astringent agent. Further, G.B. Patent No. 1570361 (published on Jul. 2, 1980) discloses a germicidal bath salt for the skin which contains a halogenated hydroxyphenyl ether and a basic carrier. However, these bath medicine compositions do not provide a lasting, persistent effect, even though they exhibit a body deodorant effect.

SUMMARY OF THE INVENTION

Accordingly, one object of the present invention is to provide a bath medicine composition which comprises a specific germicide and a carbon dioxide generating component and can effectively inhibit the generation of body odor.

Another object of the present invention is to provide a method for the application of a bath medicine composition comprising a specific germicide and a carbon dioxide generating component for the purpose of inhibiting the generation of body odor.

Another object of the present invention is to provide a method for inhibiting the generation of body odor with a specific germicide and a carbon dioxide generating component.

These and other objects of the present invention have been satisfied by the discovery that the generation of body odor can be effectively prevented by using, during bathing, a bath medicine composition comprising at least one germicide (A) selected from the group consisting of phenolic germicides, cationic germicides and trichlorocarbanilide, and a carbon dioxide generating component (B), a method for using the bath medicine composition to inhibit the generation of body odor, and a method for the application of the bath medicine composition.

DETAILED DESCRIPTION OF THE PREFERRED EMBODIMENTS

The present invention relates to a bath medicine composition comprising at least one germicide (A) selected from the group consisting of phenolic germicides, cationic germicides and trichlorocarbanilide, and a component capable of geneating carbon dioxide (B).

Within the context of the present invention, the term "bath medicine composition" refers to a composition which is dissolved or dispersed in cool or warm water in a bathtub prior to bathing. Generally, a bath medicine composition is used to keep the warmth of the body after bathing or to impart moistness to the skin.

The present invention further relates to a method for the application of a bath medicine composition which comprises dissolving or dispersing a bath medicine composition comprising at least one germicide (A) selected from the group consisting of phenolic germicides, cationic germicides and trichlorocarbanilide and a carbon dioxide generating component (B) in cool or warm water all at once or in portions, to give a final concentration of the germicide (A) within the range of from 0.1 to 100 ppm by weight, based on the total contents.

The present invention also relates to a method for inhibiting the generation of body odor which comprises adding at least one germicide (A) selected from the group consisting of phenolic germicides, cationic germicides and trichlorocarbanilide and a carbon dioxide generating component (B) either simultaneously or successively to cool or warm water to give a final concentration of the germicide (A) within the range of from 0.1 to 100 ppm by weight, based on the total weight of components (A) and (B) and water, dissolving or dispersing the germicide (A) and the carbon dioxide generating component (B) in the cool or warm water to give an aqueous solution or dispersion of the germicide (A) and the carbon dioxide generating component (B), and immersing all or part of the body in the aqueous solution or dispersion for 3 to 30 minutes.

The germicide (A) to be used in the present invention is at least one member selected from the group consisting of phenolic germicides, cationic germicides and trichlorocarbanilide.

Preferred examples of the phenolic germicides include phenols such as phenol, isopropylmethylphenol, p-chloro-m-cresol, resorcinol, thymol and hinokitiol; and halogenated bisphenols such as hexachlorophene and triclosan, among which isopropylmethylphenol, p-chloro-m-cresol, resorcinol, hinokitiol, hexachlorophene and triclosan are more preferred.

Preferred examples of the cationic germicides include quaternary ammonium compounds such as benzalkonium chloride and benzethonium chloride; chlorhexidine hydrochloride; chlorhexidine gluconate; and cetylpyridinium chloride. The cationic germicide is more preferably at least one member selected from the group consisting of benzalkonium chloride, benzethonium chloride, chlorhexidine hydrochloride and chlorhexidine gluconate.

Most preferred examples of the germicide to be used in the present invention include isopropylmethylphenol, hinokitiol, triclosan, benzalkonium chloride, trichlorocarbanilide and cetylpyridinium chloride.

The bath medicine composition of the present invention contains the germicide (A) preferably in an amount of 0.03 to 30% by weight (hereinafter referred to merely as "%"), still more preferably 0.03 to 15%, based on the total weight of the composition.

The carbon dioxide generating component (B) to be used in the present invention is not particularly limited but may be any compound or combination of compounnds which can generate carbon dioxide (i.e., carbonic acid gas) when dissolved or dispersed in cool or warm water. A combination of a carbonate with an acid is generally used as the component (B).

With respect to the present invention, the term "carbonate" includes not only full carbonates (normal salts) but also sesquicarbonates and hydrogencarbonates. Preferred examples of the carbonate to be used in the present invention include sodium hydrogencarbonate, sodium carbonate, sodium sesquicarbonate, potassium hydrogencarbonate, calcium carbonate, potassium carbonate, potassium sesquicarbonate, magnesium carbonate, ammonium hydrogencarbonate, ammonium carbonate and ammonium sesquicarbonate. These can be used singly or in a combination of two or more in the present invention. Among these carbonates, sodium hydrogencarbonate, sodium carbonate, sodium sesquicarbonate, calcium carbonate and magnesium carbonate are particularly preferred.

The term "acid" as used in the present invention includes not only organic and inorganic acids but also acid salts of organic acids. Preferred examples of the organic acid to be used in the present invention include linear aliphatic acids such as formic acid, acetic acid, propionic acid, butyric acid and valeric acid; dicarboxylic acids such as oxalic acid, malonic acid, succinic acid, glutaric acid, adipic acid, pimelic acid, fumaric acid and maleic acid; acidic amino acids such as glutamic acid and aspartic acid; and hydroxy acids such as glycolic acid, lactic acid, hydroxyacrylic acid, α-hydroxybutyric acid, glyceric acid, tartronic acid, malic acid, tartaric acid and citric acid, as well as acid salts of these organic acids. Preferred inorganic acids for use in the present invention include phosphoric acid, potassium dihydrogenphosphate, sodium dihydrogenphosphate, sodium sulfite, potassium sulfite, sodium pyrosulfite (sodium metabisulfite), potassium pyrosulfite (potassium metabisulfite), acid sodium hexametaphosphate, acid potassium hexametaphosphate, acid sodium pyrophosphate, acid potassium pyrophosphate and sulfamic acid. These acids can be used singly or as a mixture of two or more. Among these acids, it is particularly preferred to use an aliphatic dicarboxylic acid such as succinic acid and fumaric acid; malic acid or an acid salt thereof. Further, the use of a water-soluble solid acid is preferable.

When the bath medicine composition of the present invention contains a carbonate and an acid as the carbon dioxide generating component (B), the amount of the carbonate is preferably 5 to 80%, more preferably 10 to 70% based on the total weight of the composition, and the amount of the acid is preferably 10 to 300%, more preferably 20 to 200% based on the weight of the carbonate.

The type and amount of the carbon dioxide generating component (B) affect the pH of the aqueous solution or dispersion prepared by dissolving or dispersing the bath medicine composition in cool or warm water. It is preferred that the type and amount of the component (B) be selected so that the pH of the aqueous solution or dispersion prepared by dissolving or dispersing the bath medicine composition in cool or warm water in a concentration of 0.01% by weight falls within the range of 4 to 7, more preferably 6.0 to 6.7.

The pH of the solution or dispersion is determined as follows. Just before the determination of the pH, 5 l of a standard water at 40° C. is prepared in a 5-l beaker (For preparation of the standard water see below). A bath medicine composition (0.5 g, 0.01 w/v %) is added to the standard water and dissolved or dispersed therein.

When the bath medicine composition is in the form of a tablet, the tablet is crushed into particles of suitable sizes in a mortar and about 0.3 to 0.5 g of the particles thus obtained are accurately weighed. Then, the standard water is weighed into another 5-l beaker in an amount sufficient to provide a concentration of the bath medicine composition of 0.01 w/v %. The accurately weighed particles of the bath medicine composition are added to the standard water and dissolved or dispersed therein.

When the bath medicine composition is water-soluble, the aqueous solution thus prepared is stirred and thereafter the pH of the resulting homogeneous solution is determined according to the Japanese Pharmacopoeia, General Test Method. When the bath medicine composition is water-insoluble, a mixture comprising the standard water and the composition is sufficiently stirred and thereafter the pH of the supernatant of the resulting mixture is determined according to the Japanese Pharmacopoeia, General Test Method. The above standard water is prepared as follows: 73.36 mg of calcium chloride dihydrate is dissolved in 5 l of deionized water, followed by the dissolution of 83.83 mg of sodium hydrogencarbonate. Immediately after completion of the dissolution, carbon dioxide is blown into the aqueous solution thus obtained to adjust the pH thereof to 7.0.

In a preferred embodiment, the bath medicine composition of the present invention contains a cationic polymer (C) in addition to the above essential components (A) and (B).

Suitable examples of the cationic polymer (C) to be used in the present invention include cationic celluloses such as diethylaminated ethylcellulose, diisopropylaminated ethylcellulose and dimethylaminated ethylcellulose; cationic starch, cationic dextran, cationic dextrin, cationic polyvinylpyrrolidone, cationic guar gum, cationic polypeptide and chitosan. Among these polymers, it is more preferred to use cationic cellulose, cationic starch, cationic dextran, cationic dextrin, cationic polyvinylpyrrolidone, cationic guar gum or cationic polypeptide. In particular, it is most preferred to use cationic cellulose, cationic polyvinylpyrrolidone, cationic guar gum or cationic polypeptide.

The cationic polymer (C) to be used in a preferred embodiment of the present invention is preferably one having a degree of cationization of 0.01 to 10, more preferably 0.1 to 2. When a cationic polymer having a degree of cationization outside this range is used, the resulting bath medicine composition can be poor in body deodorant effect.

The cationic polymer (C), when present, is used in an amount of preferably 0.01 to 30%, more preferably 0.03 to 7.5%, based on the total weight of the composition.

It is believed that the cationic polymer (C) enhances the adsorption of the germicide (A) on the skin or the penetration thereof into the skin. Presumably owing to this effect, the generation of body odor is more effectively inhibited by using a bath medicine composition containing a cationic polymer (C) according to the present invention in bathing.

Among the bath medicine compositions according to the present invention, those comprising a cationic germicide, a carbon dioxide generating component and a cationic polymer are particularly preferred.

The bath medicine composition of the present invention may optionally contain one or more conventional components for bath medicine compositions. Examples of such optional components are as follows:

(1) inorganic salts, including:

sodium chloride, borax, sodium sulfate, sodium sulfide, sodium nitrate, sodium thiosulfate, sodium polyphosphate, sodium phosphate, magnesium oxide, potassium chloride, potassium sulfide, aluminum sulfate or alum;

(2) crude drugs, including:

fennel, phellodendron bark, german chamomile, cinnamon bark, safflower, peony root, ginger, calami rhizoma, cnidium rhizome, Japanese angelica root, citrus unshiu peel, atractylodes lancea rhizome, Japanese valerian, angelica dahurica root, diabetic puncture, mentha herb, hoelen, ginseng or peach leaf;

(3) colors, including:

tar colors authorized by the Ordinance of the Ministry of Health and Welfare of Japan (colors described in the Lists I and II attached to the Ordinance), such as Yellow No.4, Blue No. 1 and Yellow No. 202 (1); or natural colors authorized as food additives, such as chlorophyll, riboflavin, crocin, safflower and anthraquinone;

(4) fats and oils, including:

isopropyl palmitate, isopropyl myristate, squalane, squalene, liquid paraffin or white petrolatum;

(5) vitamins, including:

vitamin A, vitamin C, vitamin D or vitamin E;

(6) fragrances (7) other components, such as sulfur, hot spring deposit, mineral sand, powdery mica, neutral clay, parched bran, glycerol, surfactants, dispersing agents, binders, chelating agents, succharides, or other pharmaceutically necessary components.

The bath medicine composition of the present invention generally takes the form of a homogeneous mixture of the constituents. However, the constituents of the composition may be separately packed in two or more containers, if desired. The bath medicine composition of the present invention includes, for example, those wherein the germicide (A) and one or more optional components are packed in a container; the carbon dioxide generating component (B) and one or more other optional components are packed in another container; and both of the containers are packaged together.

The process for preparing the bath medicine composition of the present invention is not particularly limited, but may be any conventional one. For example, when the composition takes the form of a homogeneous mixture, it can be prepared by any process which can give a homogeneous mixture of the constituents.

The bath medicine composition of the present invention is preferably formulated into powder, tablet, granule or paste.

Prior to bathing, the bath medicine composition of the present invention is dissolved or dispersed in bath (cool or warm water) all at once or in portions, in order to give a final concentration of the germicide (A) within the range of from 0.1 to 100 ppm by weight (hereinafter referred to merely as "ppm"), preferably from 0.1 to 50 ppm, more preferably from 0.5 to 50 ppm, most preferably from 1 to 30 ppm, based on the total weight of bath medicine composition and water. That is, the bath medicine composition is used in such an amount that the amount of the germicide (A) is from 0.015 to 15 g per 150 l of bath. When the concentration of the germicide (A) is less than 0.1 ppm, no sufficient body deodorant effect will be attained, while when the concentration exceeds 100 ppm, the amount of the composition used per bath will be uneconomically large. The bath is preferably warm water at 15° to 45° C., more preferably at 38° to 42° C.

As used in the present invention, the term "in portions" includes both the case wherein an effective dose of the bath medicine composition taking the form of a homogeneous mixture is added to the bath in portions, and the case wherein the constituents separately packed in two or more containers are added to the bath successively.

Further, it is preferable that the bath medicine composition of the present invention be used in such an amount that the concentration of carbon dioxide in the bath falls within the range of 60 ppm or above. When the carbon dioxide concentration is less than 60 ppm, no sufficient body deodorant effect will be attained.

When the bath medicine composition of the present invention contains a cationic polymer (C), the composition is dissolved or dispersed in the bath in such an amount that the concentration of the polymer (C) falls within the range of preferably from 0.05 to 100 ppm, more preferably from 0.1 to 25 ppm. When the concentration of the polymer (C) is less than 0.05 ppm, no synergistic effect with the germicide (A) will be exhibited, which can result in a poor body deodorant effect, while when it exceeds 100 ppm, the amount of the composition used per bath will be uneconomically large.

The method for inhibiting the generation of body odor according to the present invention comprises adding the germicide (A) and the carbon dioxide generating component (B) simultaneously or successively to bath (cool or warm water) to give a concentration of the germicide (A) within the range of from 0.1 to 100 ppm, preferably from 0.1 to 50 ppm, more preferably from 0.5 to 50 ppm, most preferably from 1 to 30 ppm, dissolving or dispersing the germicide (A)

and the carbon dioxide generating component (B) in the bath to give an aqueous solution or dispersion of the germicide (A) and the carbon dioxide generating component (B), and immersing all or part of the body of a subject in need thereof in the aqueous solution or dispersion for 3 to 30 minutes. The bath is preferably warm water at 15° to 45° C., more preferably at 38° to 42° C.

In carrying out the method for inhibiting the generation of body odor according to the present invention, it is convenient to use the bath medicine composition of the present invention as the germicide (A) and carbon dioxide generating component (B) to be added to bath. When the method for inhibiting the generation of body odor according to the present invention is carried out by the use of the bath medicine composition of the present invention, the bath volume may be 100 to 250 l for whole-body bathing (wherein the part below the shoulder or chest is immersed), 50 to 150 l for half-body bathing (wherein the part below the waist is immersed) or 5 to 100 l for foot bathing (wherein the part below the knee is immersed).

After bathing, it is preferable that the body be slightly dried with a towel without taking any shower, though the bath may be washed off the body with a shower, if desired, without detrimentally affecting the body deodorant effect of the composition of the present invention.

According to the present invention, the generation of body odor can be effectively inhibited only by bathing in a bath containing the bath medicine composition of the present invention dissolved or dispersed therein. The method for inhibiting the generation of body odor according to the present invention can therefore dispense with troublesome operations such as coating and spraying.

Having generally described this invention, a further understanding can be obtained by reference to certain specific examples which are provided herein for purposes of illustration only and are not intended to be limiting unless otherwise specified.

EXAMPLES

The present invention will now be described in more detail by referring to the following Test Examples (Examples and Comparative Examples). In the following Test Examples, all percentages are given by weight, unless otherwise noted.

Test Example 1 (Organoleptic Evaluation)

Thirty-five male panelists were divided into groups A, B, C, D, E, F and G each composed of five panelists. Each panelist used a bath medicine composition or whole body cleaner having a formula specified in Table 1 in a predetermined manner and thereafter the foot odor of the panelist was organoleptically evaluated.

Each of the five panelists of group A cleansed his lower limb with a cleaner having a formula the same as that of the whole body cleaner of Comparative Example 4 except that triclosan was not used, and thereafter the lower limb was immersed in a bath (150 l) prepared by dissolving a dose (50 g) of the bath medicine composition of Example 1 in warm water and slightly dried with a towel. Each of the panelists of group B, C, D, E and F cleansed and immersed his lower limb in the same manner as that of group A except that the bath medicine composition of Example 1 was replaced by those (50 g) of Examples 2 and 3 and Comparative Examples 1, 2 and 3 respectively. Each of the five panelists of group G cleansed his lower limb with 5 g of the whole body cleaner of Comparative Example 4 and thereafter the lower limb was immersed in a bath containing the bath medicine composition of Comparative Example 1 in a similar manner to that of the other groups.

24 hours after immersion, the foot odor of each panelist was organoleptically evaluated according to the following criteria. The results are given in Table 2.

TABLE 1

| | | Ex. | | | | Comp. Ex. | | | unit: pt. by wt. |
| | | 1 Tableted bath medicine compn. | 2 Granular bath medicine compn. | 3 Tableted bath medicine compn. | 4 Tableted bath medicine compn. | 1 Tableted bath medicine compn. | 2 Tableted bath medicine compn. | 3 Tableted bath medicine compn. | 4 Whole body cleaner |
| --- | --- | --- | --- | --- | --- | --- | --- | --- | --- |
| Germicide (A) | triclosan | 0.5 | | | | | 0.5 | | 0.5 |
| | benzalkonium chloride | | 5.0 | | 5.0 | | | | |
| | cetylpyridinium chloride | | | 2.0 | | | | | |
| carbon dioxide generating component (B) | sodium hydrogencarbonate | 20.0 | 15.0 | 15.0 | 15.0 | 20.0 | 40.0 | 20.0 | |
| | sodium carbonate | 20.0 | 15.0 | 15.0 | 15.0 | 20.0 | 40.0 | 20.0 | |
| | succinic acid | 40.0 | 30.0 | 30.0 | 30.0 | 40.0 | | 40.0 | |
| benzoic acid | | | | | | | | 0.5 | |
| laurylphosphoric acid | | | | | | | | | 20.0 |
| triethanolamine | | | | | | | | | 30.0 |
| polyoxyethylene (13) oleyl ether | | 1.0 | 0.7 | 0.7 | 0.7 | 1.0 | 1.0 | 1.0 | 1.0 |
| cationic cellulose (dge. of cationization: 0.5) | | | | | 0.3 | | | | |
| propylene glycol | | | | | | | | | 10.0 |
| glycerol | | | | | | | | | 10.0 |
| polyethylene glycol 500 | | | | | | | | | 10.0 |
| polyethylene glycol 6000 | | 18.5 | 34.3 | 37.3 | 34.0 | 19.0 | 18.5 | 18.5 | |
| denatured alcohol | | | | | | | | | 10.0 |
| color | | proper amount | proper amount | proper amount | proper amount | proper amount | proper amount | proper amount | proper amount |
| water | | | | | | | | | balance |

TABLE 1-continued

|  | Ex. | | | | Comp. Ex. | | | unit: pt. by wt. |
|---|---|---|---|---|---|---|---|---|
|  | 1 Tableted bath medicine compn. | 2 Granular bath medicine compn. | 3 Tableted bath medicine compn. | 4 Tableted bath medicine compn. | 1 Tableted bath medicine compn. | 2 Tableted bath medicine compn. | 3 Tableted bath medicine compn. | 4 Whole body cleaner |
| germicide concn. (ppm) (bath vol.: 150 l) | 3 | 30 | 12 | 30 | 0 | 3 | 3 | | criteria for organoleptic evaluation (foot odor) score
3: strong,
2: medium,
1: weak, and
0: none.

TABLE 2

| group A | | group B | | group C | | group D | | group E | | group F | | group G | |
|---|---|---|---|---|---|---|---|---|---|---|---|---|---|
| panelist | score | panelist | score | panelist | score | panelist | score | panelist | score | panelist | score | panelist | score |
| $A_1$ | 0 | $B_1$ | 0 | $C_1$ | 0 | $D_1$ | 3 | $E_1$ | 1 | $F_1$ | 2 | $G_1$ | 3 |
| $A_2$ | 1 | $B_2$ | 1 | $C_2$ | 0 | $D_2$ | 2 | $E_2$ | 2 | $F_2$ | 2 | $G_2$ | 3 |
| $A_3$ | 1 | $B_3$ | 1 | $C_3$ | 1 | $D_3$ | 2 | $E_3$ | 2 | $F_3$ | 2 | $G_3$ | 2 |
| $A_4$ | 0 | $B_4$ | 1 | $C_4$ | 0 | $D_4$ | 3 | $E_4$ | 2 | $F_4$ | 3 | $G_4$ | 3 |
| $A_5$ | 0 | $B_5$ | 1 | $C_5$ | 1 | $D_5$ | 2 | $E_5$ | 1 | $F_5$ | 2 | $G_5$ | 3 |
| average | 0.4 | average | 0.6 | average | 0.4 | average | 2.4 | average | 1.6 | average | 2.2 | average | 2.8 |
| SD* | ±0.5 | SD* | ±0.5 | SD* | ±0.5 | SD* | ±0.5 | SD* | ±0.5 | SD* | ±0.4 | SD* | ±0.4 |

*SD: standard deviation

Test Example 2

Thirty-five male panelists were divided into groups A, B, C, D, E, F and G each composed of five panelists. Each of the panelists of groups A, B, D, E, F and G cleansed and immersed his lower limb in the same manner as that of Test Example 1 respectively. Each of the panelists of group C cleansed and immersed his lower limb in the same manner as that of Test Example 1 except that the bath medicine composition of Example 4 was used instead of that of Example 3.

After the immersion, the lower limb was slightly dried with a towel, immediately immersed in 3 l of warm water, and mildly rubbed therein with a sponge. Washing of the panelist was put in a 5-l beaker and allowed to stand at 40° C. for 24 hours. Then, the turbidity of the resulting washing was measured with a POIC integrating sphere turbidimeter.

The results are given in Table 3.

It can be understood from the results of Test Example 1 given in Table 2 that the generation of uncomfortable body odor such as foot odor can be inhibited for a lengthened time by bathing using the bath medicine composition of the present invention (Examples 1 to 3, groups A, B and C) as compared with (a) bathing using a bath medicine composition which contains the germicide according to the present invention but does not generate carbon dioxide (Comparative Example 2, group E), (b) bathing using a bath medicine composition which generates carbon dioxide but does not contain any germicide (Comparative Example 1, group D) or (c) bathing using a bath medicine composition which generates carbon dioxide and contains a germicide other than the specific germicides according to the present invention (Comparative Example 3, group F). Further, it can also be understood that the generation of uncomfortable body odor such as foot odor can be inhibited for a lengthened time by bathing (groups A, B and C) using the bath

TABLE 3

| group A | | group B | | group C | | group D | | group E | | group F | | group G | |
|---|---|---|---|---|---|---|---|---|---|---|---|---|---|
| panelist | turb- idity | panelist | turb- idity | panelist | turb- idity | panelist | turb- idity | panelist | turb- idity | panelist | turb- idity | panelist | turb- idity |
| $A_1$ | 1.2 | $B_1$ | 2.0 | $C_1$ | 1.9 | $D_1$ | 3.9 | $E_1$ | 3.0 | $F_1$ | 3.7 | $G_1$ | 5.0 |
| $A_2$ | 2.0 | $B_2$ | 1.4 | $C_2$ | 1.0 | $D_2$ | 3.7 | $E_2$ | 2.9 | $F_2$ | 3.2 | $G_2$ | 3.7 |
| $A_3$ | 0.9 | $B_3$ | 1.9 | $C_3$ | 0.9 | $D_3$ | 4.5 | $E_3$ | 2.6 | $F_3$ | 4.3 | $G_3$ | 4.1 |
| $A_4$ | 1.5 | $B_4$ | 1.3 | $C_4$ | 1.2 | $D_4$ | 4.8 | $E_4$ | 2.2 | $F_4$ | 4.5 | $G_4$ | 3.5 |
| $A_5$ | 1.9 | $B_5$ | 1.7 | $C_5$ | 1.5 | $D_5$ | 3.4 | $E_5$ | 3.3 | $F_5$ | 3.9 | $G_5$ | 4.8 |
| average | 1.50 | average | 1.66 | average | 1.30 | average | 4.06 | average | 2.80 | average | 3.92 | average | 4.22 |
| SD* | ±0.46 | SD* | ±0.30 | SD* | ±0.41 | SD* | ±0.58 | SD* | ±0.42 | SD* | ±0.51 | SD* | ±0.66 |

*SD: standard deviation medicine composition of the present invention (Examples 1 to 3) even when the cleansing of lower limb prior to the bathing is conducted with a whole body cleaner not containing any germicide, as compared with the case (groups G) wherein the lower limb is cleansed with a whole body cleaner (Comparative Example 4) which contains a germicide according to the present invention but does not generate carbon dioxide and thereafter immersed in a bath containing a bath medicine composition (Comparative Example 1) which generates carbon dioxide but does not contain any germicide.

As described above, the generation of foot odor, tragomaschalia, and sweat odor can be inhibited for a long time by using the bath medicine composition of the present invention (Examples 1 to 3).

Further, as apparent from the results of Test Example 2 given in Table 3, the turbidity of washings of lower limbs can be lowered by preliminary bathing using the bath medicine composition of the present invention (Examples 1, 2 and 4), which means that the bath medicine composition of the present invention has a high germicidal activity against bacteria on the skin, causative of body odor.

This application is based on Japanese Patent Application No. 6-118062 filed on May 31, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is::

1. A bath medicine composition comprising at least one germicide (A) selected from the group consisting of phenolic germicides, cationic germicides and trichlorocarbanilide, and a carbon dioxide generating component (B), wherein component B comprises a carbonate and an acid.

2. The bath medicine composition as claimed in claim 1, wherein the phenolic germicide is at least one member selected from the group consisting of phenol, isopropylmethylphenol, p-chloro-m-cresol, resorcinol, thymol, hinokitiol, hexachlorophene and triclosan.

3. The bath medicine composition as claimed in claim 2, wherein the phenolic germicide is at least one member selected from the group consisting of isopropylmethylphenol, p-chloro-m-cresol, resorcinol, hinokitiol, hexachlorophene and triclosan.

4. The bath medicine composition as claimed in claim 1, wherein the cationic germicide is at least one member selected from the group consisting of benzalkonium chloride, benzethonium chloride, chlorhexidine hydrochloride, chlorhexidine gluconate and cetylpyridinium chloride.

5. The bath medicine composition as claimed in claim 4, wherein the cationic germicide is at least one member selected from the group consisting of benzalkonium chloride, benzethonium chloride, chlorhexidine hydrochloride and chlorhexidine gluconate.

6. The bath medicine composition as claimed in claim 1, wherein the carbon dioxide generating component (B) comprises at least one member selected from the group consisting of full carbonates, hydrogencarbonates and sesquicarbonates of alkali metals; full carbonate, hydrogencarbonate and sesquicarbonate of ammonium; and full carbonates of alkaline earth metals, and at least one member selected from the group consisting of organic acids, inorganic acids and acid salts of organic acids.

7. The bath medicine composition as claimed in claim 1, wherein the germicide (A) is present in an amount of 0.03 to 30% by weight based on the total weight of the composition, wherein the carbonate is present in an amount of 5 to 80% by weight based on the total weight of the composition, and wherein the acid is present in an amount of 10 to 300% by weight based on the weight of the carbonate.

8. The bath medicine composition as claimed in claim 1, which further comprises a cationic polymer (C).

9. The bath medicine composition as claimed in claim 8, wherein the cationic polymer (C) is at least one member selected from the group consisting of cationic cellulose, cationic starch, cationic dextran, cationic dextrin, cationic polyvinylpyrrolidone, cationic guar gum and cationic polypeptide.

10. The bath medicine composition as claimed in claim 8, wherein the cationic polymer (C) is present in an amount of 0.01 to 30% by weight based on the total weight of the composition.

11. A method for the application of a bath medicine composition, which comprises dissolving or dispersing a bath medicine composition comprising at least one germicide (A) selected from the group consisting of phenolic germicides, cationic germicides and trichlorocarbanilide and a carbon dioxide generating component (B) in cool or warm water all at once or in portions, sufficient to give a final concentration of the germicide (A) within the range of from 0.1 to 100 ppm by weight, wherein component B comprises a carbonate and an acid.

12. The method for the application of a bath medicine composition as claimed in claim 11, wherein the bath medicine composition is dissolved in warm water at 15° to 45° C.

13. A method of inhibiting the generation of body odor which comprises adding at least one germicide (A) selected from the group consisting of phenolic germicides, cationic germicides and trichlorocarbanilide and a carbon dioxide generating component (B) either simultaneously or successively to cool or warm water to give a final concentration of the germicide (A) within the range of from 0.1 to 100 ppm by weight, dissolving or dispersing the germicide (A) and the carbon dioxide generating component (B) in the cool or warm water to give an aqueous solution or dispersion of the germicide (A) and the carbon dioxide generating component (B), and immersing all or part of a subject in need thereof in the aqueous solution or dispersion for 3 to 30 minutes, wherein component B comprises a carbonate and an acid.

14. The method for inhibiting the generation of body odor as claimed in claim 13, wherein the bath medicine composition is dissolved in warm water at 15° to 45° C.

* * * * *